United States Patent
Ruggeri et al.

(10) Patent No.: US 8,232,394 B2
(45) Date of Patent: Jul. 31, 2012

(54) PYRROLO[2,3-D]PYRIMIDINE DERIVATIVES; THEIR INTERMEDIATES AND SYNTHESIS

(75) Inventors: Sally Gut Ruggeri, Waterford, CT (US); Joel M. Hawkins, Old Lyme, CT (US); Teresa M. Makowski, Salem, CT (US); Jennifer L. Rutherford, Easton, PA (US); Frank J. Urban, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 549 days.

(21) Appl. No.: 11/996,899

(22) PCT Filed: Jul. 17, 2006

(86) PCT No.: PCT/IB2006/002048
§ 371 (c)(1),
(2), (4) Date: Aug. 11, 2011

(87) PCT Pub. No.: WO2007/012953
PCT Pub. Date: Feb. 1, 2007

(65) Prior Publication Data
US 2011/0288297 A1 Nov. 24, 2011

Related U.S. Application Data

(60) Provisional application No. 60/704,011, filed on Jul. 29, 2005.

(51) Int. Cl.
*C07D 487/04* (2006.01)
(52) U.S. Cl. ............................................. 544/280
(58) Field of Classification Search .................. 544/280; 546/185
See application file for complete search history.

(56) References Cited

U.S. PATENT DOCUMENTS

| 6,627,754 | B2 | 9/2003 | Blumenkopf et al. |
| 7,417,055 | B2 * | 8/2008 | Cannizzaro et al. ......... 514/306 |
| 7,432,370 | B2 * | 10/2008 | Wilcox et al. ................. 544/280 |
| 2004/0012627 | A1 | 1/2004 | Zakharia et al. |

FOREIGN PATENT DOCUMENTS

| JP | 07010877 | 1/1995 |
| WO | WO/02/096909 | 12/2002 |
| WO | WO/03/048162 | 6/2003 |
| WO | WO/2004/021979 | 3/2004 |

OTHER PUBLICATIONS

Patent Abstracts of Japan, vol. 1995, No. 04 (1995).
Saxena et al, J. Med. Chem., vol. 31, pp. 1501-1506 (1998).
Barlocco et al, Tetrahedron, Elsevier Science Pub., vol. 51, No. 42, pp. 11547-11556 (1995).
Kazimierczuk et al., J. Am. Chem. Soc., vol. 106, pp. 6379-6382 (1984).
Ripin et al, Organic Proc. Research and Dev., vol. 7, No. 1, pp. 115-120 (2003).
Cai et al, Org. Proc. Research and Dev., vol. 9, No. 1, pp. 51-56 (2005).
Glorius et al, Agnew. Chem. Int. Ed., 43:2859 (2004).
Legault et al, J. Am. Chem. Soc., 127:8966 (2005).

* cited by examiner

*Primary Examiner* — Kamal Saeed
*Assistant Examiner* — Kristin Bianchi
(74) *Attorney, Agent, or Firm* — A. David Joran

(57) ABSTRACT

This invention relates to methods and intermediates useful for the synthesis of pyrrolo[2,3-d]pyrimidine compounds. Specifically novel synthetic methods and intermediates for the synthesis of 3-{(3R,4R)-4-methyl-(7H-pyrrolo[2,3-d]pyrimidin-4-yl)-amino}-piperidin-1-yl)-3-oxo-propionitrile and its corresponding citrate salt are disclosed.

1 Claim, No Drawings

PYRROLO[2,3-D]PYRIMIDINE DERIVATIVES; THEIR INTERMEDIATES AND SYNTHESIS

This application is a National Stage Application of International Application No. PCT/IB2006/002048 filed Jul. 17, 2006, published in the English language on Feb. 1, 2007, as WO 2007/012953, which claims the benefit of U.S. Provisional Patent Application No. 60/704,011 filed on Jul. 29, 2005.

FIELD OF INVENTION

The present invention relates to methods of synthesizing pyrrolo[2,3-d]pyrimidine compounds and intermediates useful in their synthesis.

BACKGROUND

Pyrrolo[2,3-d]pyrimidine compounds are potent inhibitors of protein kinases such as the enzyme Janus Kinase 3 (JAK 3) and are therefore useful for the treatment of a wide variety of immunological disorders. Such disorders include but are not limited to lupus, multiple sclerosis, rheumatoid arthritis, psoriasis, Type 1 diabetes and complications from diabetes, cancer, asthma, atopic dermatitis, autoimmune thyroid disorders, ulcerative colitis, Crohn's disease, Alzheimer's disease and leukemia. The compounds are also useful in the treatment and prevention of chronic or acute organ transplant rejection (allografts and xenograft).

Specific pyrrolo[2,3-d]pyrimidine compounds, their methods of use, and their synthesis and intermediates have previously been described in U.S. Pat. No. 6,627,754, WO 02096909, WO 03048162 and US published application 2004/0102627A1 commonly assigned to the assignee of the present invention, all of which are incorporated by reference in their entirety. U.S. Pat. No. 6,627,754 describes the compound 3-{4-methyl-(7H-pyrrolo[2,3-d]pyrimidin-4-yl)-amino}-piperidin-1-yl)-3-oxo-propionitrile and its corresponding citrate salt as useful inhibitors of protein kinases (such as the enzyme JAK 3) and as such are useful for therapy as immunosuppressive agents for organ transplants, xeno transplantation, lupus, multiple sclerosis, rheumatoid arthritis, psoriasis, Type 1 diabetes and complication from diabetes, cancer, atopic dermatitis, autoimmune thyroid disorders, ulcerative colitis, Crohn's disease, Alzheimer's disease, leukemia and other indications where immune suppression would be desirable. US published application 2004/0102627A1 describes the synthesis of an intermediate, cis-(1-benzyl-4-methyl-piperidin-3-yl)-methyl-amine hydrochloride salt, which is useful in the synthesis of 3-{(3R,4R)-4-methyl-(7H-pyrrolo[2,3-d]pyrimidin-4-yl)-amino}-piperidin-1-yl)-3-oxo-propionitrile and its corresponding citrate salt.

SUMMARY OF THE INVENTION

Previous syntheses of pyrrolopyrimidine compounds described above and specifically 3-{(3R,4R)-4-methyl-(7H-pyrrolo[2,3-d]pyrimidin-4-yl)-amino}-piperidin-1-yl)-3-oxo-propionitrile have all suffered from poor yields and slow reaction times for the coupling of 4-chloro pyrrolo pyrimidine with nucleophiles, specifically with (3R,4R)-(1-benzyl-4-methyl-piperidine-3-A-methylamine and its salts. It has been surprisingly found that the introduction of a removable activating group on the pyrrolo pyrimidine nucleus with a leaving group at the 4 position markedly improves yields and reaction times towards reactions with nucleophiles specifically (3R,4R)-(1-benzyl-4-methyl-piperidine-3-yl)-methylamine and its salts. The synthesis of a key intermediate useful in implementing one aspect of the aforementioned synthetic sequence, 2,4-dichloro-7H-pyrrolo[2,3-d]pyrimidine, has been previously described (Saxena, S. K., et al., J. Med. Chem., 31, 1501, 1988; 26.5% reported yield; WO 04021979; 41% reported yield). However, the synthesis described in the literature produced low yields of the desired product. It has now been surprisingly found that by carefully controlling the amounts of phosphorous oxychloride and trialkyl amine base used to react with the starting material, 7H-pyrrolo[2,3-d]pyrimidine-2,4 diol, one can obtain significantly improved yields of the desired product.

Prior attempts at the asymmetric hydrogenation of pyridinium salts without attached chiral auxiliaries (Glorius, F., et al., Angew, Chem. Int. Ed., 43, 2859, 2004 and references cited therein; see also Legault, C. Y., et al., J. Am. Chem. Soc. 127, 8966, 2005; both of which are incorporated by reference in their entireties) have typically resulted in piperidine formation but with poor enantiomeric excesses (ee's). It has been surprisingly found that the asymmetric hydrogenation of suitably substituted N-benzyl or substituted N-benzyl pyridinium salts or suitably substituted N-benzyl or substituted N-benzyl tetrahydropyridines with certain asymmetric hydrogenation catalysts produces enantiomerically enriched piperidine derivatives useful in the synthesis of the pyrrolopyrimidine compounds described above and specifically 3-{(3R,4R)-4-methyl-(7H-pyrrolo[2,3-d]pyrimidin-4-yl)-amino}-piperidin-1-yl)-3-oxo-propionitrile.

As embodied and broadly described herein, this invention, in one aspect relates to methods of making a compound of the Formula IVa.

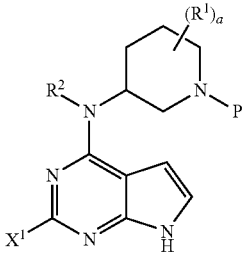

IVa comprising the step of;
coupling an activated pyrrolo pyrimidine compound of the Formula IIa

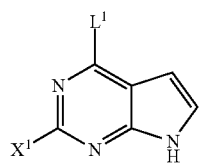

IIa wherein $L^1$ is a leaving group, preferably chloro, bromo, iodo, or fluoro, most preferably chloro, and $X^1$ is an activating group, preferably chloro, bromo, iodo, fluoro, $CO_2R'$, $COCO_2R'$; $SO_2Ar$, and $COAr$ where Ar is a $(C_3-C_{12})$ aromatic group optionally including 1 to 6 heteroatoms chosen from O, NR' and S optionally substituted with 1 to 3 groups selected from $(C_1-C_6)$alkyl, halogen, nitro, and cyano; where R' is chosen from the group consisting of $(C_1-C_6)$alkyl and benzyl; most preferably $X^1$ is chloro; with an amine of the Formula IIIa, or a salt thereof;

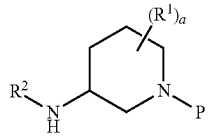

IIIa wherein $R^1$ is hydrogen or $(C_1-C_6)$alkyl; a is an integer from 0 to 4; $R^2$ is hydrogen or $(C_1-C_6)$ alkyl; and P is a nitrogen protecting group, preferably benzyl; in the presence of a base, preferably an alkali or trialkyl amine base, more preferably potassium carbonate or sodium carbonate, most preferably potassium carbonate, to afford a coupled product of the Formula IVa.

In another embodiment the step above further comprises the step of; removing the activating group, preferably chloro, and nitrogen protecting group, preferably benzyl, from a compound of the formula IVa

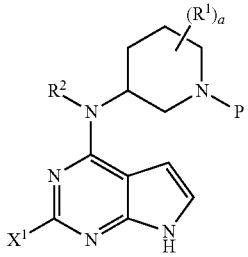

IVa sequentially, in either order, or in a single reaction vessel, to afford a compound of the Formula V

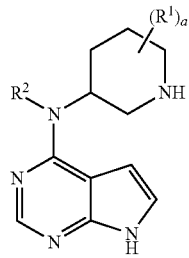

V

In a further embodiment the removal of the activating group when the activating group is chloro and protecting group when the protecting group is labile to hydrogenolysis, preferably benzyl or substituted benzyl, is accomplished in a single reaction vessel in the presence of hydrogen or a hydrogen source and a catalyst, preferably palladium hydroxide, palladium on carbon and platinum on carbon, most preferably palladium hydroxide.

In a further embodiment the amine of the Formula IIIa or a salt thereof is IIIb or IIIc racemic or enantiomerically enriched mixture thereof.

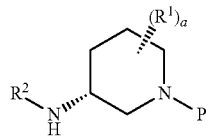

IIIb

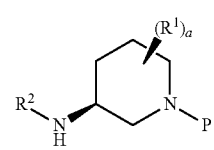

IIIc

In a further embodiment the amine of the Formula IIIs or a salt thereof is IIId or IIIe or a racemic or enantiomerically enriched mixture thereof.

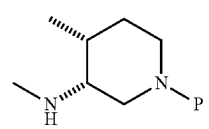

IIId

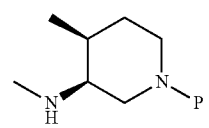

IIIe

In a further embodiment the amine of the formula Ma or a salt thereof has the formula IIId which has the 3R,4R configuration,

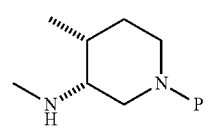

IIId

In a further embodiment the amine salt of the Formula IIId having the 3R,4R configuration has the Formula IIIf.

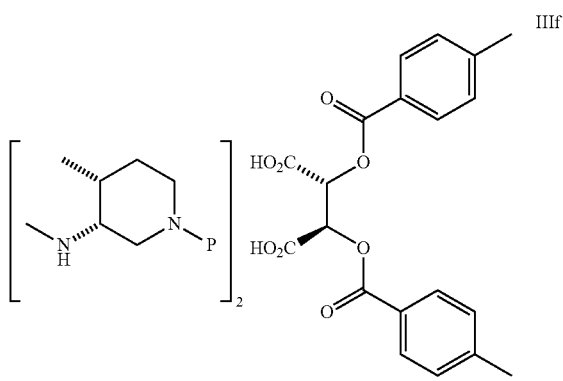

IIIf

In a further embodiment P in Formulas IIIb-f is protecting group labile to hydrogenolysis, preferably benzyl or substituted benzyl.

In a further embodiment the compound of the Formula IVa has the Formula IVb

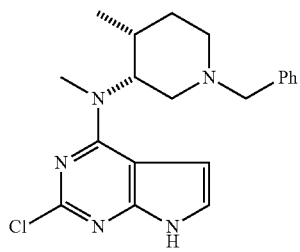

In a further embodiment the removal of the chloro activating group and N-benzyl protecting group from a compound of the formula IVb is accomplished in a single reaction vessel in the presence of hydrogen or a hydrogen source, and a hydrogenation catalyst, preferably palladium hydroxide, palladium on carbon, or platinum on carbon, most preferably palladium hydroxide, to afford a compound of the Formula Va.

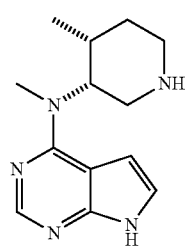

In a further embodiment the compound of Formula Va is acylated with an acylating agent of the Formula VI

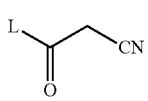

wherein L is a leaving group chosen from the group consisting of —OCOR$^3$, OR$^3$, halogen, hydroxyl succinimidyl, sulfonates such as tosyl and mesyl; wherein R$^3$ is C$_1$-C$_6$ alkyl; preferably L is —OCOR$^3$, wherein R3 is t-butyl; optionally in the presence of a base, to afford a compound of the Formula Ia.

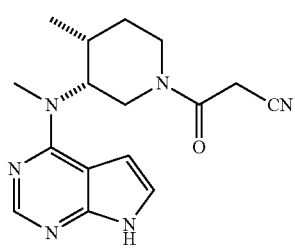

Additional coupling reagents and conditions for amide formation between activated and unactivated carboxylic acid derivatives and amines which are suitable for the above acylation step can be found in Benz, G *Comprehensive Organic Synthesis*, B. Trost Ed., Volume 6, Chapter 2.3, tables 1-7 which is herein incorporated by reference in its entirety.

In a further embodiment a compound of the Formula Ia is reacted with citric acid to afford the corresponding citric acid salt.

A further embodiment of the present invention is a method of making a compound of the Formula IVb

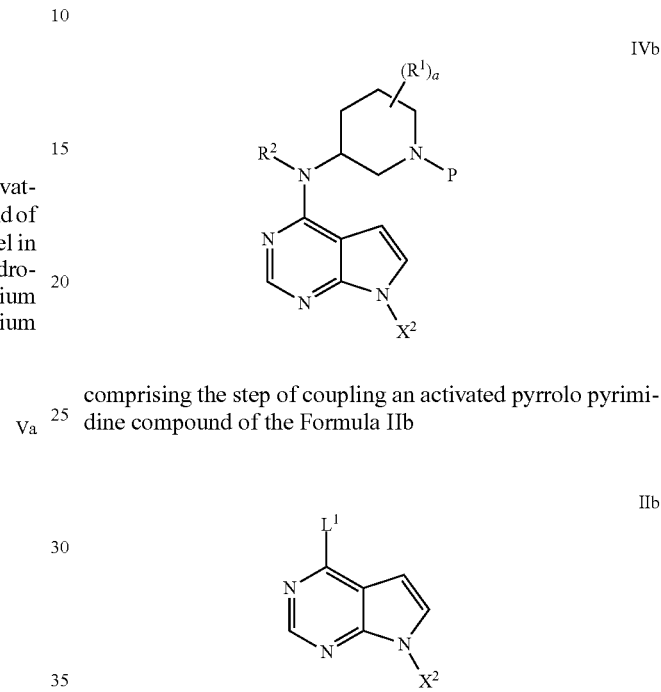

comprising the step of coupling an activated pyrrolo pyrimidine compound of the Formula IIb

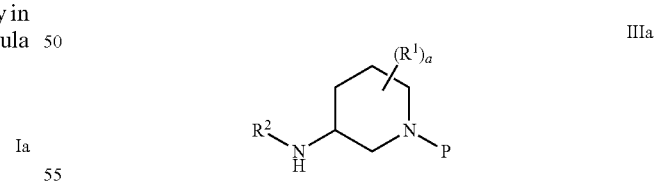

wherein L$^1$ is a leaving group, preferably chloro, iodo, bromo and fluoro, most preferably chloro and X$^2$ is an activating group, preferably benzyl, SO$_2$Ar, CO$_2$R', and COAr; Ar is a O$_3$-C$_{12}$ aromatic group optionally including 1 to 6 heteroatoms chosen from O, NR' and S, optionally substituted with 1 to 3 groups selected from (C$_1$-C$_6$)alkyl, halogen, nitro, and cyano; where R' is chosen from the group consisting of (C$_1$-C$_6$)alkyl and benzyl; preferably X$^2$ is a tosyl group (p-toluene sulfonyl group; —SO$_2$C$_6$H$_4$CH$_3$); with an amine of the Formula IIIa, or a salt thereof,

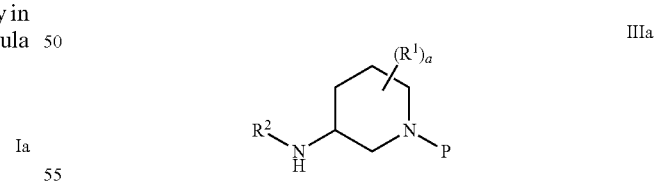

wherein R$^1$ is (C$_1$-C$_6$) alkyl; a is an integer from 0 to 4; R$^2$ is hydrogen or (C$_1$-C$_6$) alkyl; and P is a nitrogen protecting group, preferably benzyl; in the presence of a base, preferably an alkali or trialkyl amine base, more preferably potassium carbonate or sodium carbonate, most preferably potassium carbonate, to afford a coupled product of the Formula IVb.

In a further embodiment, when X$^2$ is a tosyl group, the tosyl group and nitrogen protecting group are removed from a compound of the Formula IVb sequentially in either order or in a single reaction vessel to afford a compound of the Formula V

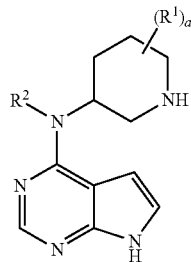

V

In a further embodiment the tosyl group is removed by an aqueous alkali base, preferably aqueous sodium hydroxide.

In a further embodiment the amine of the Formula IIIa or a salt thereof is Formula IIIb or IIIc or a racemic or enantiomerically mixture thereof.

IIIb

IIIc

In a further embodiment the amine of the Formula IIIa or a salt thereof is IIId or IIIe or mixtures thereof.

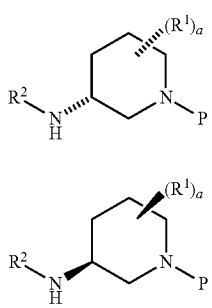

IIId

IIIe

In a further embodiment the amine of the formula IIIa or a salt thereof has the formula IIId which has the 3R,4R configuration.

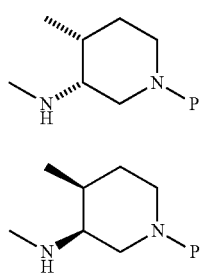

IIId

In a further embodiment the amine salt of the Formula IIId which has the 3R,4R configuration has the Formula IIIf.

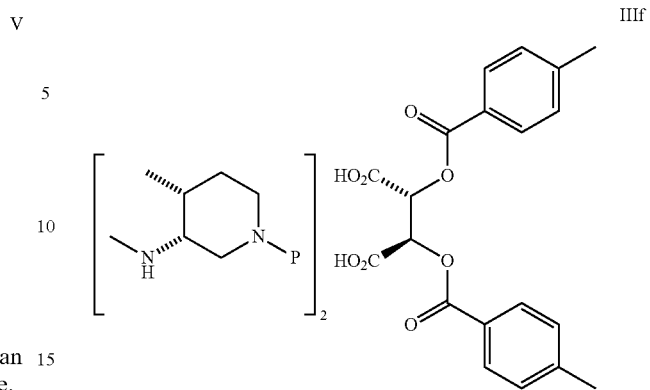

IIIf

In a further embodiment P in Formulas IIIb-f is a protecting group labile to hydrogenolysis, preferably benzyl.

In a further embodiment Formula IVb has the Formula IVc

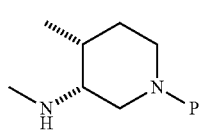

IVc

In a further embodiment the removal of the tosyl group and benzyl group of the Formula IVc is accomplished by an aqueous alkali base to remove the tosyl group and by hydrogen or a hydrogen source and a catalyst preferably palladium hydroxide, palladium on carbon, platinum on carbon, most preferably palladium hydroxide, optionally in the presence of an acid, preferably acetic acid, to remove the benzyl group, to afford a compound of the Formula Va Va Removal of the tosyl group and benzyl group may be accomplished in either order.

In yet another embodiment of the present invention is a method for the synthesis of 2,4-dichloro-7H-pyrrolo[2,3-d] pyrimidine comprising the steps of:
  a) reacting 7H-pyrrolo[2,3-d]pyrimidine-2,4 diol with phosphorus oxychloride in an aromatic solvent, preferably toluene, to form a first solution at a first temperature, preferably from between about 0° C. to about 50° C., most preferably about 25° C.;
  b) increasing said first temperature of the first solution to a second temperature, preferably between about 40° C. to about 100° C., most preferably about 75° C.;

c) adding to said first solution at the second temperature a tertiary amine base preferably diisopropylethylamine, to form a second solution at the second temperature and;
d) increasing said second temperature of the second solution to a third temperature, preferably between about 75° and about 125° C., most preferably about 105° C., for a first interval of time preferably between about 1 hr and about 24 hr, most preferably about 16 hr;
wherein the phosphorous oxychloride is present in between about 1.5 and about 6 equivalents and the tertiary amine base, preferably diisopropylethylamine, is present in between about 1.0 and about 8.0 equivalents; both relative to the starting 7H-pyrrolo[2,3-d]pyrimidine-2,4 diol. Preferably the phosphorous oxychloride is present in between about 2.0 and about 3 equivalents and the tertiary amine base is present in between about 1.1 and about 2 equivalents. Most preferably the phosphorous oxychloride is present in about 3.0 equivalents and the tertiary amine base is present in about 2.0 equivalents.

In a further embodiment a method of producing enantiomerically enriched piperidines of the Formula Xc;

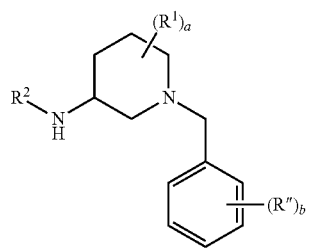

wherein $R^1$ is hydrogen or $(C_1-C_5)$alkyl; a is an integer from 0 to 4; $R^2$ is hydrogen or $(C_1-C_6)$alkyl; and R'' is chosen from the group consisting of hydrogen, $C_1-C_6$ alkyl and $CF_3$ groups; b is an integer from 0 to 4; comprising the step of;
a) asymmetrically hydrogenating a benzyl pyridinium salt of the Formula Xd

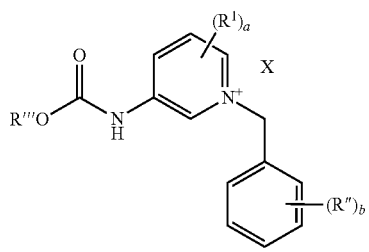

wherein where X— is selected from the group consisting of chloro, bromo, fluoro, iodo, Vitiate, tosylate or —$BF_4$, preferably bromo, R''' is $C_1-C_6$ alkyl; with a rhodium, iridium, or ruthenium catalyst preferably bis(1,5-cyclooctadiene)rhodium (I) trifluoromethanesulfonate and a chiral phosphine ligand preferably (R)-(−)-1-{(S)-2-(diphenyl phosphino)ferrocenyl]ethyl di-t-butylphosphine; (R)-(−)-1-{(S)-2-(dicyclohexyl phosphino)ferrocenyl]ethyl di-t-butylphosphine, or R)-(−)-1-{(S)-2-di-(p-trifluoromethyl phenyl)phosphino)ferrocenyl]ethyl di-t-butylphosphine in the presence of hydrogen or a hydrogen source is provided.

Further preferred is where the benzyl pyridinium salt has the Formula Xe

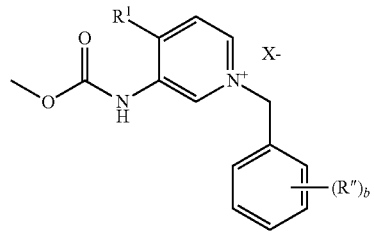

Further preferred is where the benzyl pyridinium salt has the Formula Xf

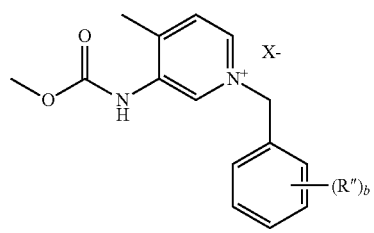

In a further embodiment a method of producing enantiomerically enriched piperidines of the Formula Xg

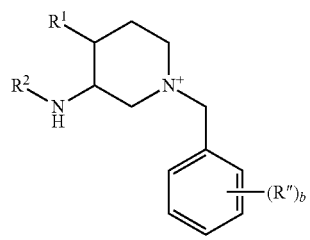

wherein $R^1$ is hydrogen or $(C_1-C_6)$alkyl; $R^2$ is $C_1-C_6$ alkyl; and R'' is chosen from the group consisting of hydrogen, $C_1-C_6$ alkyl and $CF_3$ groups; b is an integer from 0 to 4; comprising the step of:
a) Asymmetrically hydrogenating a tetrahydropyridine of the Formula Xh

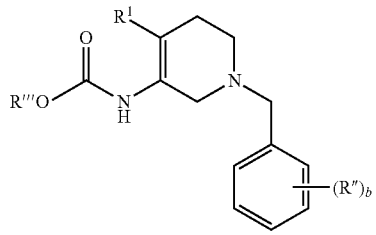

wherein R''' is $C_1-C_6$alkyl; with a rhodium, iridium, or ruthenium catalyst preferably bis(1,5-cyclooctadiene) rhodium (I) trifluoromethanesulfonate and a chiral phosphine ligand preferably (R)-(−)-1-{(S)-2-(diphenyl phosphino)ferrocenyl]ethyl di-t-butylphosphine; (R)-(−)-1-{(S)-2-(dicyclohexyl phosphino)ferrocenyl]ethyl di-t-butylphosphine, or (R)-(−)-1-{(S)-2-di-(p-trifluoromethyl phenyl)phosphino)ferrocenyl]ethyl di-t-butylphosphine in the presence of hydrogen or a hydrogen source.

Further preferred is where the tetrahydropyridine has the Formula XI

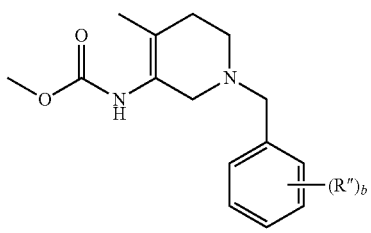

The present invention may be understood more readily by reference to the following detailed description of exemplary embodiments of the Invention and the examples included therein.

In this specification and in the claims that follow, reference will be made to a number of terms that shall be defined to have the following meanings:

The term "alkyl" includes saturated monovalent C1-C20 hydrocarbon radicals having straight branched or cyclic moieties or combinations thereof. Examples of such groups include but are not limited to methyl, ethyl, propyl, isopropyl, butyl, isobutyl, t-butyl, cyclopropyl, cyclobutyl, cyclopentyl, and cyclohexyl.

The term "alkoxy" includes O-alkyl groups wherein alkyl is as defined above. Examples include but are not limited to methoxy, ethoxy, propoxy, isopropoxy, butoxy, isobutoxy, t-butoxy, cyclopropoxy, cyclobutoxy, and cyclopentoxy.

The term "halo" or "halogen" includes fluoro, chloro, bromo, or iodo.

The term "alkenyl" includes monovalent straight branched or cyclic hydrocarbon radicals containing one or more double bonds. Examples include but are not limited to, ethenyl, propenyl, butenyl, isobuteneyl, cyclopentenyl and cyclohexenyl.

The term "alkynyl" includes monovalent straight or branched hydrocarbon radicals containing one or more triple bonds. Examples include but are not limited to ethynyl, propynyl, and butynyl.

The term "acyl" refers to a —C(O)— moiety.

The term "nitrogen protecting group" or "amino protecting group" as used herein will be understood by the skilled person to include those mentioned in "Protective Groups in Organic Synthesis" $2^{nd}$ Edition, T. W. Greene and P. G. M, Wutz, Wiley Interscience (1991) in particular those indexed at pages 218-222 of that reference, the disclosure of which document is hereby incorporated by reference in its entirety. Examples of suitable protecting groups include but are not limited to benzyl, carbobenzyloxy, t-butoxy carbonyl (BOC) 9-fluorenyl-methylenoxy carbonyl and allyloxycarbonyl.

The term "leaving group" as used herein represents a group that can be displaced by nucleophiles. Examples of leaving groups include but are not limited to halogen, mesyloxy, tosyloxy, and anhydride residues of carbonic acids such as t-butoxy-carbonyloxy.

The term "activating group" refers to any group on pyrrolo pyrimidlne moieties of the present invention which enhances its reactivity toward addition elimination type reactions with nucleophiles. Activating groups are typically electron withdrawing groups such as halogens, for example chloro, sulfonates for example tosylates, mesylates and the like, esters, carbonates, carbamates, and acyl derivatives. Also included are benzyl derivatives.

The term "acids" is taken to mean inorganic and organic acids. Inorganic acids include but are not limited to hydrochloric, hydrobromic, phosphoric, metaphosphoric, nitric and sulfuric. Organic Acids include but are not limited to tartaric, acetic, methane-sulfonic, trifluoroacetic, citric, maleic, lactic, fumaric, benzoic, succinic, methanesulfonic, oxalic and p-toluene sulfonic acids.

The term 'bases' is taken to mean inorganic and organic bases. Inorganic bases include but are not limited to sodium carbonate, potassium carbonate, lithium hydroxide, sodium hydroxide, potassium hydroxide, lithium carbonate, sodium carbonate, potassium carbonate, lithium hydride, potassium hydride, sodium hydride, lithium hydrogen carbonate, sodium hydrogen carbonate, and potassium hydrogen carbonate. Organic bases include but are not limited to metal alkoxides, metal-alkyl complexes, pyridine, alkyl amines, dialkylamines and trialkylamines. Examples of alkyl, dialkyl and trialkyl amines include but are not limited to methyl amine, dimethyl amine, triethyl amine and diisopropyl ethyl amine. Also included are cyclic amines such as DBU. Examples of metal alkoxides include but are not limited to sodium methoxide, potassium methoxide, sodium t-butoxide, potassium t-butoxide and sodium ethoxide. Metal alkyl complexes include but are not limited to alkyl lithium reagents such as n butyl lithium, see butyl lithium and t-butyl lithium. Also included in this definition are Grignard Reagents such as phenyl magnesium bromide and ethyl magnesium bromide.

The acids which are used to prepare the pharmaceutically acceptable acid addition salts of the aforementioned compound of the Formula Ia which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate, [i.e., 1,1'-methylene-bis-(2-hydroxy-3-naphthoate)]salts.

The term tertiary amine refers to C1-C8 trialkyl amines. Examples include but are not limited to triethyl amine, diisoproplyethyl amine, and trimethylamine. Also included in this definition is pyridine.

The term "about" as used herein means plus or minus 10% for each of the numerical units.

The term "enantiomeric excess" (ee) as used herein means the excess of one of the two enantiomers over the other, generally as a percentage. Therefore an enantiomeric excess of 90% corresponds to the presence of 95% of one enantiomer and of 5% of the other in the mixture in question.

The term "enantiomerically enriched" means that one enantiomer is present in excess relative to the other. That is to say one enantiomer represents greater than 50% of the mixture. Also included in this definition are single enantiomers (i.e. 100% ee).

The term substituted benzyl refers to a benzyl group substituted on the phenyl ring by one or more group chosen from $C_1$-$C_6$ alkyl, —$CF_3$, OMe, $NO_2$ and CN.

The term "psi" refers to pounds per square inch.

The term (C3-C12) aryl optionally substituted with 1 to 6 heteroatoms includes but is not limited to phenyl, naphthyl, pyrldyl, quinolinyl, benzofuranyl, benzothiofene, indole and the like.

The term "hydrogen source" refers to any source of hydrogen that may be generated in situ. In the case of phase-transfer hydrogenation, formic acid and salts thereof such as ammonium formiate, alkaline metal formiates, and the like may be used as hydrogen sources.

DETAILED DESCRIPTION OF THE INVENTION

The following reaction Schemes illustrate the preparation of the compounds of the present invention. Unless otherwise indicated all R groups, L, $X^1$, $X^2$ and P groups in the reaction Schemes and the discussion that follows are as defined as above.

Scheme I
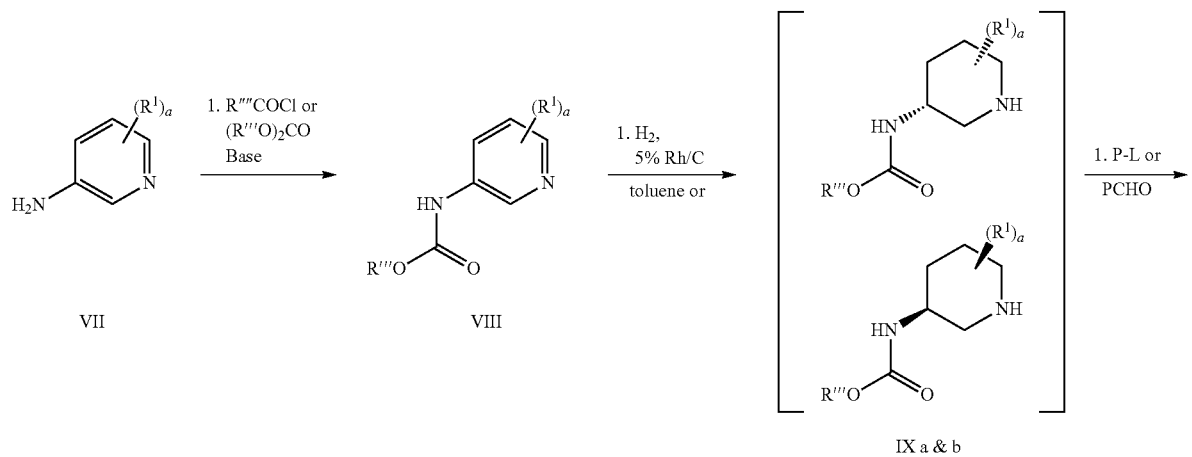
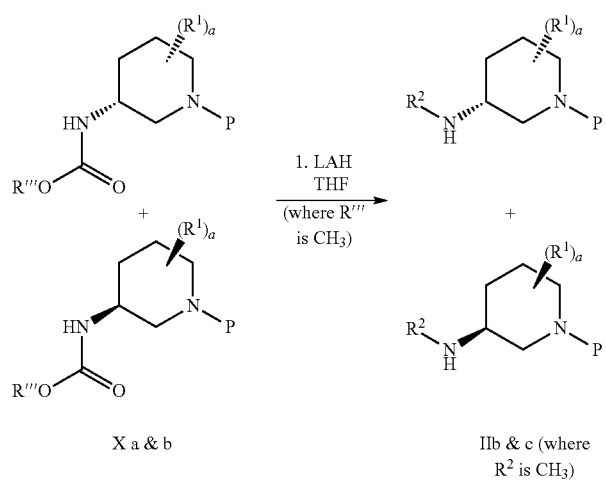
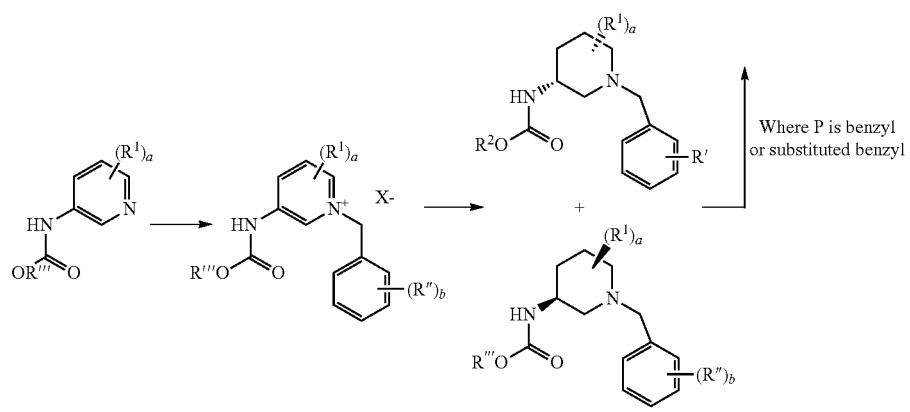

-continued
or

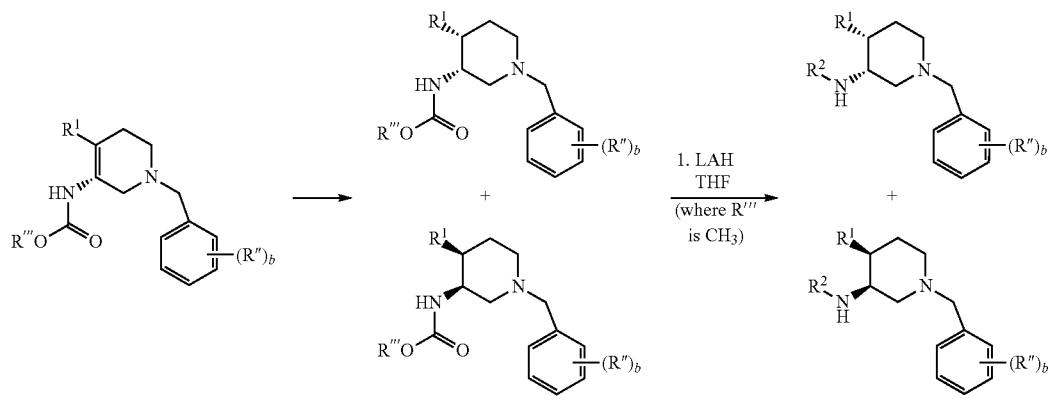

A suitably substituted 3-aminopyridine of the formula VII can be reacted with a dialkyl carbonate or alkylchloroformate to obtain VIII. VIII can then reduced in the presence of hydrogen preferably under a pressurized hydrogen atmosphere, preferably between about 70 to about 80 psi, and 5% rhodium on carbon or rhodium on alumina in the presence of an acid, preferably acetic acid, at an elevated temperature of between about 50° C. and about 150° C., preferably 70-80° C., to afford the cis-piperidinyl carbamates IXa and b. The piperidinyl nitrogen can then be protected by reacting IXa and b with a suitable protecting reagent to afford Xa and b. (see "Protective Groups in Organic Synthesis" $2^{nd}$ Edition, T. W. Greene and P. G. M. Wutz, Wiley Interscience (1991) for examples). For example a reagent such as P-L, where P is the protecting group and L is a leaving group can be reacted, in the presence of a base such as potassium or sodium carbonate, with the piperidinyl nitrogen of IXa and b to afford the N-protected cis piperidinyl carbamate Xa and b. Alternatively the aldehyde PCHO where P is the protecting group, can be reacted under hydrogenation conditions with the piperidinyl nitrogen. Reaction conditions can be determined by one of ordinary skill in the art depending upon the protecting group employed. The carbamate group of Xa and b can then be reduced using a suitable reducing agent, for example, lithium aluminum hydride, in an ethereal solvent such as THF, at a reduced temperature of between about −78° C. to about 70° C., typically 70° C., to afford IIIb and c (where $R^2$ is methyl). Alternatively the carbamate group of Xa and b can be cleaved by hydrolysis and the resulting free amine can then be reacted with various alkylating agents, for example $R^2$-L where L is a leaving group, in a polar aprotic solvent such as dimethyl formamide (DMF), optionally in the presence of a base such as a trialkylamine base, to afford intermediates IIIb and c.

Alternatively either a benzyl or substituted benzyl pyridinium salt of the Formula VIIIa where X— is chloro, bromo, fluoro, iodo, triflate, tosylate or —BF$_4$, preferably bromo; and where R" is chosen independently for each position capable of substitution from hydrogen, $C_1$-$C_6$alkyl or CF$_3$ groups or a suitably substituted tetrahydropyridine derivative where R" is as stated above, may be subjected to the asymmetric hydrogenation conditions such as with a rhodium, iridium or ruthenium catalyst and a chiral phosphine ligand, including monophosphine and bisphosphine ligands. Examples of appropriate chiral phosphine ligands can be found in Chem Rev 2003, 103, 3029 herein incorporated by reference in its entirety. The preferred catalysts are those formed from bis(1, 5-cyc(ooctadiene)rhodium (I) trifluoromethanesulfonate and a chiral Josiphos-type ligand. These preferred ligands can be purchased commercially from Solvias (Basel Switzerland). Preferred reagents and conditions to accomplish the transformation are bis(1,5-cyclooctadiene)rhodium (1) trifluoromethanesulfonate and (R)-(−)-1-{(S)-2-(diphenyl, dicyclohexyl or di-(p-trifluoromethyl phenyl)phosphino) ferrocenyl]ethyl di-t-butylphosphines in the presence of a pressurized hydrogen atmosphere, preferably between about 50 and about 200 psi, in an solvent, preferably a THF ethanol mixture, at an elevated temperature preferably between about 50 C and about 70 C; resulting in enantiomerically enriched piperidine Xa (for example 50-70% ee Xa over Xb). The enriched Xa so produced could be carried on and subsequently used in the chiral resolution step infra or may be used to couple directly to the activated pyrrolopyrimidine after the formation of II b and c (ie formation of enantiomerically enriched IIb).

Mixtures of $R^1$ substituted cis and trans 3 amino piperidines (IIIa) may be synthesized from suitably substituted N-protected-piperidin-3-ones, prepared by the methods of Iorio, M. A. and Damla, G.; Tetrahedron, Vol. 26: p. 55-59 (1970) and Grieco, et al., Journal of the American Chemical Society, Vol. 107: p. 1768 (1985). Both references are incorporated by reference in their entireties modified using 5% methanol as co-solvent, by reaction with $R^2$—NH$_2$ acetic acid, and sodium triacetoxy borohydride according to the procedure described in Example 1 of the US published application 2004/0053947 which is also incorporated by reference in its entirety. Piperidines of the Formula IIIa may be used in any of the subsequent couplings with activated pyrrolo pyrimidines to produce coupled products as mixtures of all possible diastereomers.

Scheme II

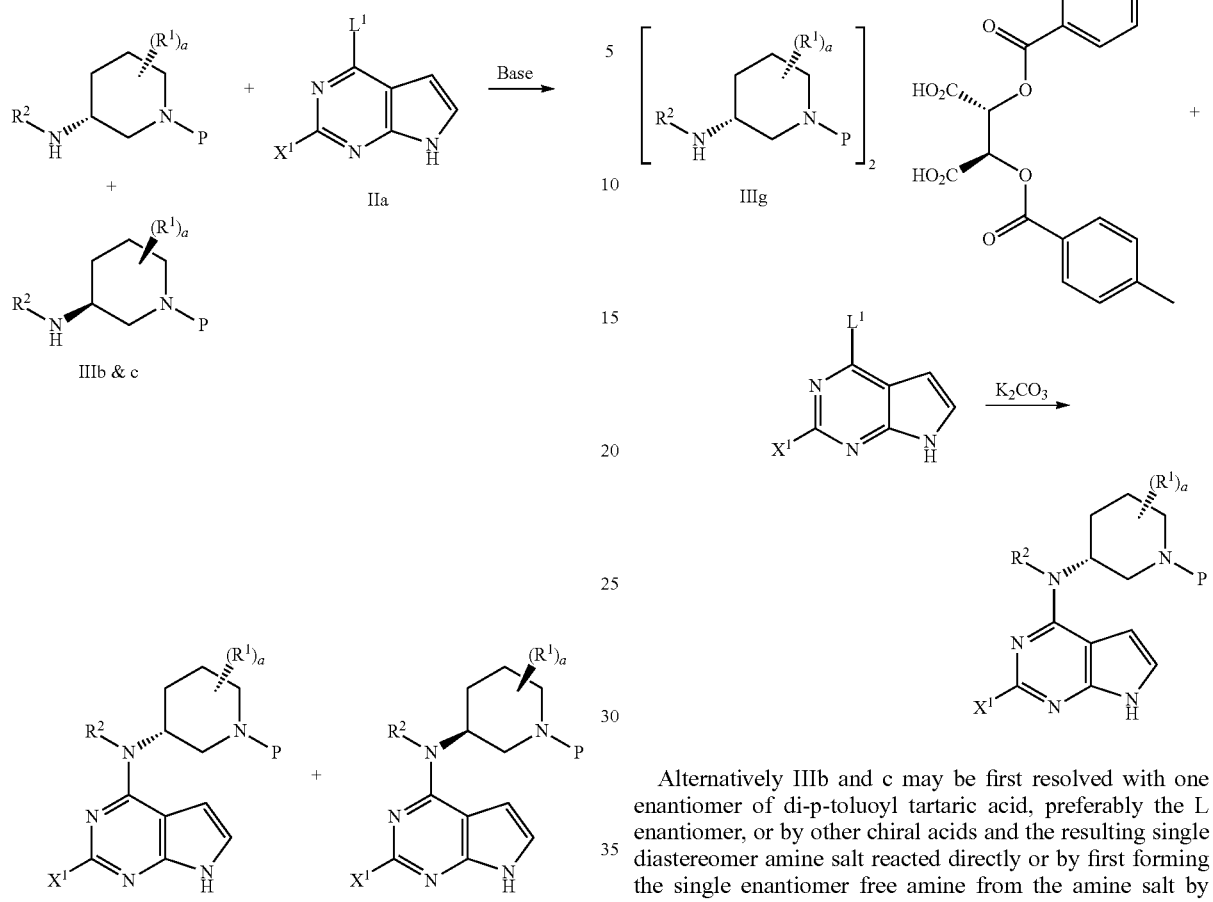

Cis N-protected 3-amino piperidines IIIb and c can then be coupled with the activated pyrrolo pyrimidine of the formula IIa in the presence of a base such as potassium or sodium carbonate in a polar solvent or mixture of polar solvents such as water or water and acetonitrile or DMSO (dimethylsulfoxide), at an elevated temperature of between about 50° C. and about 150° C., preferably 100° C., to afford the coupled product IVa.

Scheme III

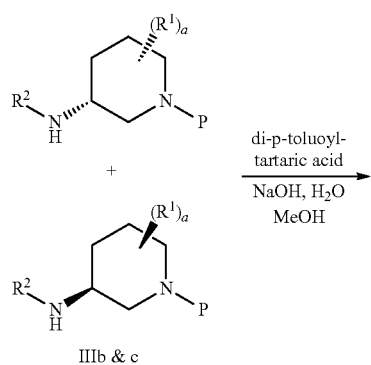

Alternatively IIIb and c may be first resolved with one enantiomer of di-p-toluoyl tartaric acid, preferably the L enantiomer, or by other chiral acids and the resulting single diastereomer amine salt reacted directly or by first forming the single enantiomer free amine from the amine salt by reaction with aqueous base such as aqueous sodium hydroxide, with the activated pyrrolo pyrimidine IIa in the presence of a base in a solvent or mixture of polar solvents such as water or water and acetonitrile or DMSO, at an elevated temperature of between about 50° C. and about 150° C., preferably 100° C., to afford IVa as a single enantiomer. (For alternate resolution methods see Jacques, J, et al., "Enantiomers, Racemates and Resolutions", Wiley, N.Y., 1981; herein incorporated by reference un its entirety)

Scheme IV

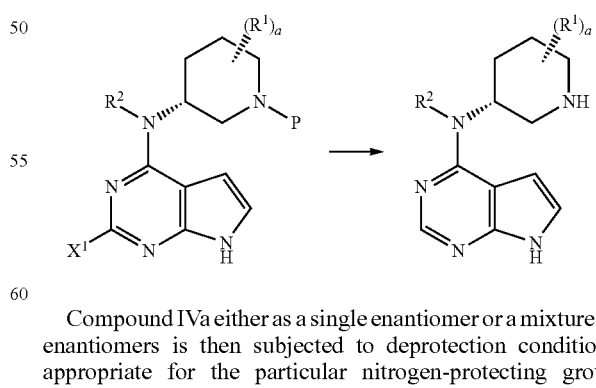

Compound IVa either as a single enantiomer or a mixture of enantiomers is then subjected to deprotection conditions appropriate for the particular nitrogen-protecting group employed. Typically these deprotecting conditions will also remove the activating group to form a compound of the Formula V. For example, when P is a group labile to hydrogenolysis and $X^1$ is chloro the protecting group and activating group may be removed by hydrogen or a hydrogen source in the presence of a catalyst. Preferably the conditions which can be employed are pressurized hydrogen, typically 50 psi, and a hydrogenation catalyst such as Pd(OH)$_2$, in a polar solvent such as water optionally in the presence of an acid such as acetic acid or HCl. Alternatively either the protecting group or activating group may be removed first using one set of conditions followed by removal of the remaining group under a second set of conditions.

Scheme V

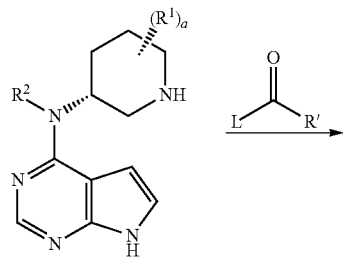

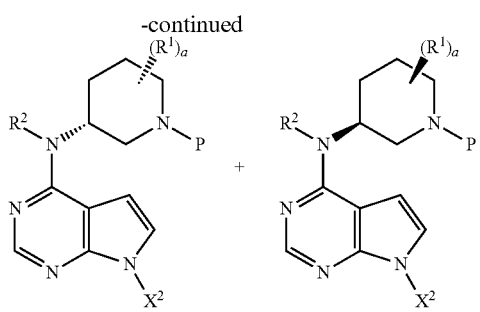

Alternatively an activated pyrrolo pyrimidine of the Formula IIb can be coupled to the cis N-protected 3 amino piperidine IIIb & c, produced according to the methods described in Scheme 1, in the presence of a base in a polar solvent or mixture of polar solvents such as water or water and acetonitrile at an elevated temperature of between about 50° C. and about 150° C., preferably 100° C., to afford the coupled product IVb as a mixture of enantiomers.

Scheme VII

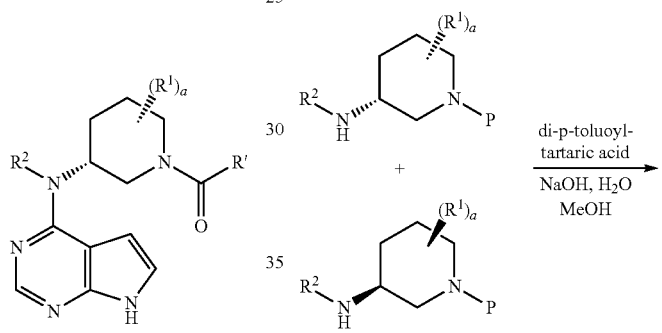

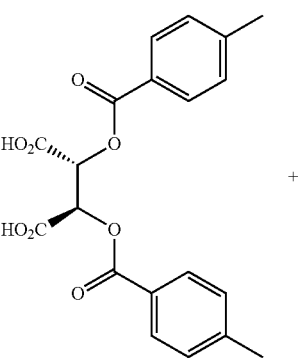

The piperidinyl nitrogen of the compound of the Formula V may be acylated using an acylating agent of the Formula VII and L is a leaving group, optionally in the presence of a base such as a trialkylamine base, in a polar protic or aprotic solvent such as methylene chloride to afford a compound of the Formula VII. The compound of the Formula VII may be converted to a pharmaceutically acceptable salt by the action of an organic acid such as citric, hydrochloric and the like. Optionally the pharmaceutically acceptable salt of the compound of Formula VII may be recrystallized from an organic solvent or mixtures of organic solvents.

Scheme VI

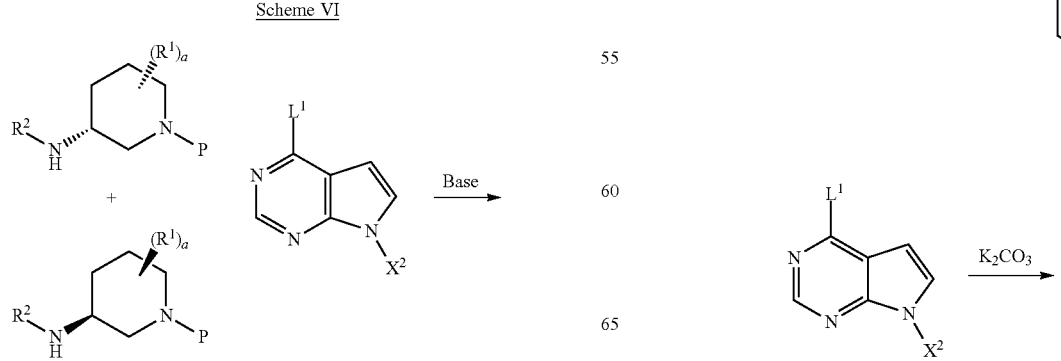

-continued

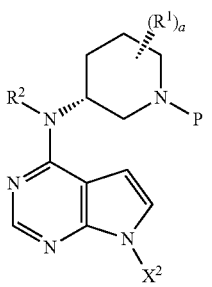

Alternatively IIIb & c, produced according to the methods described in Scheme 1, may be first resolved with one enantiomer of di-p-toluoyl tartaric acid, preferably the L enantiomer, or by other chiral acids using standard resolution techniques i.e. crystallization of a single diastereomer salt and the resulting single diastereomer amine salt reacted directly or by first forming the single enantiomer free amine from the amine salt by reaction with aqueous base such as aqueous sodium hydroxide, with the activated pyrrolopyrimidine IIb, in the presence of a base such as sodium or potassium carbonate, in a polar solvent or mixture of polar solvents such as water or water and methanol at an elevated temperature of between about 50° C. and about 150° C., preferably 100° C., to afford IVb as a single enantiomer. (For alternate resolution methods see Jacques, J, et al., "Enantiomers, Racemates and Resolutions, Wiley, N.Y., 1981; herein incorporated by reference in its entirety).

Scheme VIII

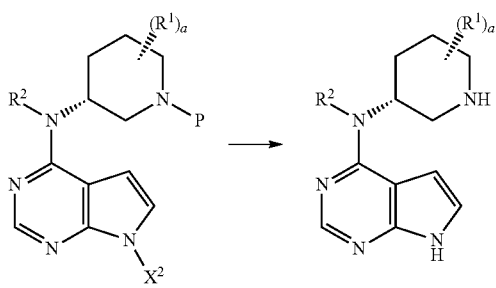

Coupled product IVb is then subjected to deprotection conditions appropriate for the particular nitrogen protecting group and conditions to remove the tosyl activating group. When the protecting group is a group labile to hydrogenolysis hydrogenating conditions maybe employed such as hydrogen pressurized to 10-100 psi, and a hydrogenation catalyst such as $Pd(OH)_2$ in a polar solvent or mixture polar solvents such as a mixture of isopropyl alcohol and water optionally in the presence of an acid such as acetic or hydrochloric acid, to remove nitrogen protecting group followed by an alkali base, for example, such as aqueous sodium hydroxide to remove the activating group when the activating group is tosyl, to afford a compound of the Formula V. When both the activating group and the protecting group are labile to hydrogenolysis both may be removed by hydrogenation conditions in a single reaction vessel. Alternatively either the protecting group or activating group may be removed first using one set of conditions followed by removal of the remaining group under a second set of conditions.

The compound of the Formula V so produced may be further reacted as previously described.

EXPERIMENTAL

Example 1

Preparation of Enriched-(3R,4R)-(1-benzyl-4-methyl-piperidine-3-yl)-methylamine via Asymmetric Hydrogenation Step A. Preparation of 1-benzyl-3-methoxycarbonylamino-4-methyl-pyridinium bromide to a clean, dry, nitrogen purged 500 mL flask were added (4-methyl-pyridin-3-yl)-carbamic acid methyl ester (25.0 g, 150 mmol), toluene (250 ml) and benzyl bromide (28.3 g, 165 mmol). The reaction was heated to 110° C. for at least 20 hours. After cooling to between 20-25° C. the reaction was filtered and the resulting solids washed with toluene (100 ml). After drying under vacuum for at least 12 hours between 40-50° C. with a slight nitrogen bleed (1-benzyl-4-methyl-pyridin-3-yl)-carbamic acid methyl ester bromide (48.6 g, 144 mmol) was isolated in 96.1% yield (greater than 95% purity by NMR).

To a suitably sized reaction vessel were added 1-benzyl-3-methoxycarbonylamino-4-ethyl-pyridinium bromide (150 mg, 0.446 mmoles), bis(1,5-cyclooctadiene)rhodium (I) trifluoromethanesulfonate (11 mg, 0.0223 mmoles available from Strem Chemical Co. Newburyport, Mass.) and (R)-(−)-1-[(S)-2-(diphenylphosphino)ferrocenyl]ethyldi-t-butylphosphine (32 mg, 0.033 mmoles—available from Solvias, Basel, Switzerland). The solids were purged with nitrogen (5× at 90 psi) then degassed THF (2 ml) and degassed ethanol (1 ml) were added. The mixture was purged with nitrogen (5× at 90 psi) followed by hydrogen (1× at 210 psi). The reaction mixture was heated to 70° C. then pressurized with hydrogen to 200 psi. After 48 h, the mixture was cooled to 30° C. and purged with nitrogen (5× at 90 psi). An aliquot was removed for GCMS analysis.

Sample preparation: 100 μL aliquot of reaction mixture is diluted in 1 mL MeOH. Add 10 μL triethylamine. Mix. Filter off precipitates. Analyze on GC MS (column Cyclosil B, temperature gradient 140-240° C., 2 degrees per minute) GC MS analysis: 84% cis product 68% ee, 2% trans product, 4% debenzylation byproduct, 3% alkene intermediate)

Alternatively, chiral HPLC may also be used for the analysis. Analysis performed on Agilent 1100 system: HPLC conditions: Daicel Chiralcel OJ 4.6 mm×250 mm analytical column, 5% Ethanol/hexanes, flow 1 ml/min, 210 nm, 20 minute run.

Example 2

Preparation of 1-benzyl-4-methyl-1,2,5,6-tetrahydro-pyridin-3-yl)-carbamic acid methyl ester Benzyl chloride (2.1 mL, 18.3 mmol) was added to a slurry of (4-methyl-pyridin-3-yl)-carbamic acid methyl ester (3.16 g, 19.0 mmol) in toluene (15 mL) at 80° C. A homogenous reaction mixture resulted after 10 minutes and then solids precipitated after 30 minutes. The slurry was stirred at 80° C. for 16 hours then cooled to room temp. The solids were filtered and washed with toluene. After drying, the product was isolated as a gray solid (4.17 g, 78%).

To a reaction mixture of 1-benzyl-3-methoxycarbonylamino-4-methyl-pyridinium chloride (4.0 g, 13.0 mmol) in EtOH (ethanol) (20 mL) was added sodium borohydride (0.645 g, 17.0 mmol). Gas evolution was observed and the reaction was exothermic. The reaction mixture was stirred at room temp. for 16 hours. The reaction was quenched with $H_2O$ (10 mL), filtered through Celite and the Celite pad was washed with EtOH (2×10 mL). The solvent volume was reduced in vacuo. The resulting mixture was basified to pH 9 with 1 N sodium hydroxide then extracted with MTBE (methyl t butyl ether) (2×15 mL). The combined organic layers were washed with $H_2O$ (10 mL), dried (sodium sulfate), and concentrated to a yellow oil (2.44 g, 72%).

Example 3

Preparation of enriched (3R,4R)-(1-benzyl-4-methyl-piperidine-3-yl)methylamine via Asymmetric Hydrogenation of 1-benzyl-4-methyl-1,2,5,6-tetrahydro-pyridin-3-yl)-carbamic acid methyl ester To the reaction vessel were added 1-benzyl-4-methyl-1,2, 5,6-tetrahydro-pyridin-3-yl)-carbamic acid methyl ester (150 mg, 0.577 mmoles), bis(1,5-cyclooctadiene)rhodium (I) trifluoromethanesulfonate (13 mg, 0.0288 mmoles—available from Strem Chemical Co. Newburyport, Mass.) and (R)-(−)-1-[(S)-2-(dicyclohexylphosphino)ferrocenyl]ethyldi-t-butylphosphine (32 mg, 0.033 mmoles—available from Solvias, Basel Switzerland). The solids were purged with nitrogen (5× at 90 psi) then degassed THF (2 ml) and degassed ethanol (1 ml) were added. The mixture was purged with nitrogen (5× at 90 psi) followed by hydrogen (1× at 210 psi). The reaction mixture was heated to 70° C. then pressurized with hydrogen to 200 psi. After 48 h, the mixture was cooled to 30° C. and purged with nitrogen (5× at 90 psi). An aliquot was removed for GCMS analysis. GC MS analysis: 97% cis product 66% ee, 2% trans product. Same analysis by GCMS or chiral HPLC as described above.

Example 4

Synthesis of 3-{(3R,4R)-4-methyl-(7H-pyrrolo[2,3-d]pyrimidin-4-yl)-amino}-piperidin-1-yl)-3-oxo-propionitrile Preparation of bis-(3R,4R)-(1-benzyl-4-methyl-piperidine-3-yl)-methylamine di-p-toluoyl-L-tartaric acid To a clean, dry, nitrogen-purged 250 ml flask were charged racemic cis-(1-benzyl-4-methyl-piperidine-3-yl)-methylamine bis hydrochloride (20.0 g, 68.7 mmol), di-p-toluoyl-L-tartaric acid (L-DPTT) (15.9 g, 41.2 mmol) and methanol (100 ml). A solution of sodium hydroxide (5.5 g, 137.3 mmol in water (100 ml)) was added to the reaction at a rate to maintain the temperature below 30° C. The reaction was heated to between 70-80° C. and held at this temperature for at least 60 minutes. The reaction was cooled to 5-15° C. over at least 4 hours and held at this temperature for at least 12 hours. The solids were filtered and washed with a 1:1 mixture of MeOH:water (60 ml). The wet-cake was returned to the 250 ml flask and methanol (100 ml) and water (100 ml) were charged. The reaction was heated to between 70-80° C. and held at this temperature for at least 120 minutes. The reaction was cooled to 5-15° C. over at least 4 hours and held at this temperature for at least 12 hours. The solids were filtered and washed with a 1:1 mixture of MeOH:water (60 ml). The wet-cake was sampled for purity (99.4% ee) to ensure an additional repulp was not necessary. After drying under vacuum at 40-50° C. for at least 24 hours with a slight nitrogen bleed, the title compound (11.9 g, 28.9 mmol) was isolated in 42.1% yield (98.6% enantiomeric excess, 0.63% trans isomer by GC (Cyclosil B column 30 m×I.D. 0.25 mm; Inlet Temp 250; 2.0 ml/min flow rate; 15 min run; 160 C isothermal method.

Example 5

Preparation of N-[(3R,4R)-1-benzyl-4-methylpiperidin-3-yl]-2-chloro-N-methyl-7H-pyrrolo[2,3-d]pyrimidin-4-amine (Formula IVb)

To a clean, dry, nitrogen-purged 500 ml reactor were charged 2,4-dichloro-7H-pyrrolo[2,3-d]pyrimidine, prepared as described below, (20.0 g, 0.106 mol), bis-(3R,4R)-(1-benzyl-4-methyl-piperidine-3-yl)-methylamine di-p-toluoyl-L-tartaric acid (20 g, 0.106 mol), potassium carbonate (44.6 g, 0.319 mol) and water (200 ml). The reactor was heated to 95-105° C. for a minimum of 10 hours then cooled to 20-30° C. and held for a minimum of 3 hours. The resulting solids were isolated by filtration, washed with water (60 ml) and dried at 50° C. to afford 39.5 g (100%) of the title compound.

Anal. Calcd. for $C_{20}H_{24}ClN_5$: C. 64.94; H, 6.54; N, 18.93. Found: C. 64.78; H, 6.65; N, 18.83. $^1$H NMR (400 MHz, $d_6$-acetone): δ10.80 (bs, 1H), 7.36 (d, J=7.0 Hz, 2H), 7.30 (t, J=7.0 Hz, 2H), 7.24-7.20 (m, 1H), 7.13 (d, J=3.7 Hz, 1H), 6.66 (bs, 1H), 5.15 (bs, 1H), 3.69 (bs, 3H), 3.54 ($AB_q$, J=13.3 Hz, 1H), 3.50 ($AB_q$, J=13.3 Hz, 1H), 2.92 (dd, J=12.0, 5.4 Hz, 1H), 2.88-2.83 (m, 1H), 2.77 (bs, 1H), 2.64-2.59 (m, 1H), 2.29 (bs, 1H), 2.16 (bs, 1H), 1.75-1.69 (m, 2H), 0.94 (d, J=6.6 Hz, 3H). $^{13}$C NMR (400 MHz, $d_6$-DMSO, mixture of isomers): δ 158.0, 152.5, 151.8, 138.3, 129.1, 128.6, 128.1, 127.6, 126.8, 121.0, 102.3, 100.8, 62.5, 54.6, 53.1, 50.8, 35.3, 32.0, 30.9, 15.3.

Example 6

Preparation of methyl-[(3R,4R)-4-methyl-piperidin-3-yl]-(7H-pyrrolo[2,3-d]pyrimidin-4-yl)amine To a clean, dry, nitrogen-purged 500 ml hydrogenation reactor were charged 20 wt % $Pd(OH)_2$/C (palladium hydroxide on carbon) (5.0 g, 50% water wet), water (200 ml), and N-((3R,4R)-1-benzyl-4-methylpiperidin-3-yl)-2-chloro-N-methyl-7H-pyrrolo[2,3-d]pyrimidin-4-amine (50.0 g, 0.135 mol). The reactor was purged three times at 50 psi with nitrogen and three times at 50 psi with hydrogen. Once purging was complete, the reactor was heated to 70-75° C. and pressurized to 50 psi with hydrogen through a continuous feed. The hydrogen uptake was monitored until no hydrogen was consumed for a minimum of 1 hour. The reactor was cooled to 20-30° C. and purged three times at 50 psi with nitrogen. The reaction mixture was filtered through water-wet Celite and transferred to a clean, dry, nitrogen-purged 500 ml reactor for subsequent processing.

Example 7

Preparation of 4-chloro-7-(toluene-4-sulfonyl)-7H-pyrrolo[2,3-d]pyrimidine

To a clean, dry, nitrogen-purged reactor were charged acetone (87.5 ml), p-toluenesulfonyl chloride (17.1 g, 0.09 mol) and 4-chloro-7H-pyrrolo[2,3-d]pyrimidine (25.0 g, 0.16 mol). The reactor was cooled to between −5.0 to 5.0° C. and 2.5 M sodium hydroxide (78.1 ml) was added at a rate to maintain the temperature below 5.0° C. The reactor was warmed to between 20-30° C. and stirred for a minimum of 5 hours. The resulting solids were isolated by filtration and washed with acetone/water (1:1, 25 ml each). After drying for a minimum of 12 hours under vacuum at 40-50° C. with slight nitrogen bleed, 44.9 g (90.1%) of the title compound were isolated.

Mp 140.2-147.7° C. Anal. Calcd. for $C_{13}H_{10}ClN_3O_2S$: C, 50.73; H, 3.28; N, 13.65. Found: C, 50.50; H, 3.06; N, 13.63. $^1H$ NMR (400 MHz, $d_6$-DMSO): δ 8.79 (s, 1H), 8.09 (d, J=4.2 Hz, 1H), 8.01 (d, J=8.5 Hz, 2H), 7.43 (d, J=8.5 Hz, 2H), 6.92 (d, J=4.2 Hz, 1H), 2.32 (s, 3H). $^{13}C$ NMR (400 MHz, $d_6$-DMSO): δ 153.2, 152.7, 151.2, 147.2, 134.3, 131.0, 129.3, 128.5, 119.9, 103.9, 21.8.

Example 8

Preparation of [(3R,4R)-1-benzyl-4-methyl-piperidin-3-yl]-methyl-[7-(4-methyl-benzenesulfonyl)-7H-pyrrolo[2,3-d]pyrimidin-4-yl]amine To a clean, dry, nitrogen-purged reactor were charged 4-chloro-7-(4-methyl-benzenesulfonyl)-7H-pyrrolo[2,3-d]pyrimidine (25.12 g, 0.082 mol), bis-(3R,4R)-(1-benzyl-4-methyl-piperidine-3-yl)-methylamine di-p-toluoyl-L-tartaric acid (40.31 g, 0.041 mol), potassium carbonate (34.2 g, 0.245 mol), and water (125.6 ml). The mixture was heated to 95-105° C. for a minimum of 10 hours, then cooled to 45-55° C. Acetonitrile (25 ml) was charged and the slurry was held at 45-55° C. for a minimum of 1 hour. The mixture was further cooled to 20-30° C. and stirred for a minimum of 5 hours. The resulting solids were isolated by filtration and washed with water (50 ml). After drying, 32.8 g (82.1%) of the title compound were isolated.

Mp 181.7-184.4C. Anal. Calcd. for $C_{27}H_{31}N_5O_2S$: C, 66.231; H, 6.38; N, 14.3. Found: C, 66.04; H, 6.47; N, 14.44. $^1H$ NMR (400 MHz, $CDCl_3$): δ 8.34 (s, 1H), 8.06 (d, J=8.7 Hz, 2H), 7.43 (d, J=4.2 Hz, 1H), 7.30-7.29 (m, 6H), 7.25-7.21 (m, 1H), 6.67-6.66 (m, 1H), 5.14 (bs, 1H), 3.56-3.44 (m, 5H), 2.82-2.78 (m, 1H), 2.73 (bs, 1H), 2.58-2.55 (m, 1H), 2.38 (s, 3H), 2.31 (bs, 1H), 2.12 (bs, 1H), 1.74 (bs, 1H), 1.69-1.61 (m, 1H), 0.90 (d, J=7.0 Hz, 3H). $^{13}C$ NMR (400 MHz, $CDCl_3$): δ 158.2, 152.9, 152.1, 145.5, 138.7, 135.4, 129.9, 129.1, 128.5, 128.4 127.3, 120.8, 106.6, 106.9, 63.7, 55.5 (b), 53.0 (b), 51.8 (b), 35.9 (b), 32.8, 31.4, 217 15.9 (b).

Example 9

Preparation of [(3R,4R)-1-benzyl-4-methyl-piperidin-3-yl]-methyl-(7H-pyrrolo[2,3-d]pyrimidin-4-yl)-amine To a clean, nitrogen-purged reactor were charged 50% sodium hydroxide solution (210 ml) and (1-benzyl-4-methyl-piperidin-3-yl)-methyl-[7-(toluene-4-sulfonyl)-7H-pyrrolo[2,3-d]pyrimidin-4-yl]-amine (30.0 g, 0.061 mol). The mixture was heated to 95-105° C. for a minimum of 5 hours then cooled to 70-90° C. and water (300 ml) was added. The slurry was cooled to room temperature over a minimum of 1.5 hours and held at room temperature for 1 hour. The solids were isolated by filtration and washed with water (120.0 ml) to obtain 25.2 g of the title compound, water wet.

$^1H$ NMR (400 MHz, $CD_3OD$): δ 8.05 (s, 1H), 7.36-7.28 (m, 5H), 7.24-7.20 (m, 1H), 7.06 (d, J=3.7 Hz, 1H), 6.62 (d, J=3.7 Hz, 1H), 5.08 (bs, 1H), 3.58-3.52 (m, 5H), 2.85 (dd, J=11.2, 7.0 Hz, 1H), 2.68 (dd, J=11.2, 3.7 Hz, 1H), 2.65-2.59 (m, 1H), 2.45-2.39 (m, 1H), 2.29-2.20 (m, 1H), 1.90-1.81 (m, 1H), 1.70-1.63 (m, 1H), 0.98 (d, J=7.0 Hz, 3H). $^{13}C$ NMR (400 MHz, $d_6$-DMSO, mixture of isomers): δ 166.8, 164.4, 158.6, 156.1, 138.4, 137.9, 137.8, 136.6, 135.5, 135.3, 112.7, 110.0, 72.4, 64.3 (b), 62.4, (b), 60.3

Example 10

Preparation of methyl-[(3R,4R)-4-methyl-piperidin-3-yl]-(7H-pyrrolo[2,3-d]pyrimidin-4-yl)-amine To a clean, dry, nitrogen-purged 2 L hydrogenation reactor were charged 20 wt % $Pd(OH)_2$/C (24.0 g, 50% water wet), water (160 ml), isopropanol (640 ml), (1-benzyl-4-methyl-piperidin-3-yl)-methyl-(7H-pyrrolo[2,3-d]pyrimidin-4-yl)-amine (160.0 g, 0.48 mol), and acetic acid (28.65 g, 0.48 mol). The reactor was purged with three times at 50 psi with nitrogen and three times at 50 psi with hydrogen. Once purging was complete, the reactor was heated to 45-55° C. and pressurized to 50 psi with hydrogen through a continuous feed. The hydrogen uptake was monitored until no hydrogen was consumed for 1 hour. The reactor was cooled to 20-30° C. and purged three times at 50 psi with nitrogen. The reaction mixture was filtered through wet Celite and the filtrate was sent to a clean, dry, nitrogen-purged vessel. A solution of sodium hydroxide (39.33 g) in water (290 ml) was charged and the mixture was stirred for a minimum of 1 hour then heated to 75-90° C. The isopropanol was removed by distillation. The reaction mixture was cooled to 20-30° C. and 2-methyltetrahydrofuran (1.6 L) was added. The aqueous layer was drained off and the 2-methyltetrahydrofuran was displaced with toluene (1.6 L). The distillation was continued until the final volume was 800 ml. The slurry was cooled to 20-30° C. and held for a minimum of 7 hours. The resulting solids were isolated by filtration and washed with toluene (480 ml). After drying under vacuum between 40-50° C. for a minimum of 24 hours with a slight nitrogen bleed 102.3 g (87.3%) of the title compound were isolated.

Mp 158.6-159.8° C. $^1H$ NMR (400 MHz, $CDCl_3$): δ 11.38 (bs, 1H), 8.30 (s, 1H), 7.05 (d, J=3.5 Hz, 1H), 6.54 (d, J=3.5 Hz, 1H), 4.89-4.87 (m, 1H). 3.39 (s, 3H), 3.27 (dd, J=12.0, 9.3 Hz, 1H), 3.04 (dd, J=12.0, 3.9 Hz, 1H), 2.94 (td, J=12.6, 3.1 Hz, 1H0, 2.84 (dt, J=12.6, 4.3 Hz, 1H), 2.51-2.48 (m, 1H), 2.12 (bs, 2H), 1.89 (ddt, J=13.7, 10.6, 4 Hz, 1H), 1.62 (dq, J=13.7, 4 Hz, 1H), 1.07 (d, J=7.3 Hz, 3H). $^{13}C$ NMR (400 MHz, $CDCl_3$): δ 157.9, 152.0, 151.0, 120.0, 103.0, 102.5, 56.3, 46.2, 42.4, 34.7, 33.4, 32.4, 14.3.

Example 11

Preparation of 3-{(3R,4R)-4-methyl-3-[methyl-(7H-pyrrolo[2,3-d]pyrimidin-4-yl)-amino]-piperidin-1-yl}-3-oxo-propionitrile To a clean, dry, nitrogen-purged 1.0 L reactor were charged methyl-(4-methyl-piperidin-3-yl)-(7H-pyrrolo[2,3-d]pyrimidin-4-yl)-amine (32.0 g, 0.130 mol), toluene (160 ml), ethyl cyanoacetate (88.53 g, 0.783 mol) and triethyl amine (26.4 g, 0.261 mol). The reaction was heated to 100° C. and held for 24 hours. The reaction was washed with water (160 ml). The organic layer concentrated to a volume of 10 ml and water (20 ml) was added. The residual toluene was removed by distillation and the mixture was cooled to room temperature. Acetone (224 ml) was added followed by citric acid (27.57 g, 0.144 mol) in water (76 ml). The resulting slurry was stirred for 7 hours. The solids were isolate by filtration, washed with acetone (96 ml), and dried under vacuum to afford 42.85 g (65.3%) of the title compound.

Example 12

Alternate Preparation of 3-{(3R,4R)-4-methyl-3-[methyl-(7H-pyrrolo[2,3-d]pyrimidin-4-yl)-amino]-piperidin-1-yl}-3-oxo-propionitrile via Acid Chloride To a clean, dry, nitrogen-purged reactor were charged cyanoacetic acid (2.30 g, 27.0 mmol), methylene chloride (20 ml), oxalyl chloride (3.36 g, 26.5 mmol) and DMF (1 drop). The reaction was allowed to stir at room temperature for a minimum of 40 minutes. The reaction was then cooled to −15 to −10° C. and held. To a separate dry, nitrogen-purged reactor were added methyl-(4-methyl-piperidin-3-yl)-(7H-pyrrolo[2,3-d]pyrimidin-4-yl)-amine (1.3 g, 5.3 mmol), DMF (7 ml) and triethylamine (5.5 g, 54.0 mmol). The reaction was stirred until a homogeneous mixture was obtained. The mixture was then slowly added to the acid chloride keeping the temperature below 5° C. The reaction was allowed to stir at −10 to 5° C. for 30 minutes and then warmed to room temperature, then held for a minimum of 1 hour. Ethyl acetate (30 ml) was charged and the solution was washed with saturated sodium bicarbonate (2×30 ml). The volatiles were removed by distillation and the residue was dissolved in acetone (27 ml), and water (5 ml). Citric acid (1.02 g, 5.3 mmol) was added and the resulting solids were stirred for a minimum of 12 hours. The solids were filtered and washed with acetone (3 ml) and water (5 ml), then dried under vacuum to afford 2.0 g (74%) of the title compound.

Example 13

Preparation of 3-{(3R,4R)-4-methyl-3-[methyl-(7H-pyrrolo[2,3-d]pyrimidin-4-yl}-amino]-piperidin-1-yl)-3-oxo-propionitrile citrate salt To a clean, dry, nitrogen-purged 500 ml reactor were charged methyl-(4-methyl-piperidin-3-yl)-(7H-pyrrolo[2,3-d]pyrimidin-4-yl)-amine (25.0 g, 0.102 mol) and methylene chloride (250 ml). The mixture was stirred at room temperature for a minimum of 2.5 hours. To a clean, dry, nitrogen-purged 1 L reactor were charged cyanoacetic acid (18.2 g, 0.214 mol), methylene chloride (375 ml), and triethyl amine (30.1 ml, 0.214 mol). The mixture was cooled to −15.0-5.0° C. over one hour and trimethylacetyl chloride (25.6 ml, 0.204 mol) was added at a rate to maintain the temperature below 0° C. The reaction was held for a minimum of 2.5 hours, then the solution of the amine was added at a rate that maintained the temperature below 0° C. After stirring for 1 hour, the mixture was warmed to room temperature and 1M sodium hydroxide (125 ml) was added. The organic layer was washed with water (125 ml) The methylene chloride solution was displaced with acetone until a volume of 500 ml and a temperature of 55-65° C. had been achieved. Water (75 ml) was charged to the mixture while maintaining the temperature at 55-65° C. A solution of citric acid (20.76 g, 0.107 mol) in water (25.0) was charged and the mixture was cooled to room temperature. The reactor was stirred for a minimum of 5 hours and then the resulting solids were isolated by filtration and washed with acetone (2×75 ml), which was sent to the filter. The salt was charged into a clean, dry, nitrogen-purged 1 L reactor with 2B ethanol (190 ml) and water (190 ml). The slurry was heated to 75-85° C. for a minimum of 4 hours. The mixture was cooled to 20-30° C. and stirred for an additional 4 hours. The solids were isolated by filtration and washed with 2B ethanol (190 ml). After drying in a vacuum oven at 50° C. with a slight nitrogen bleed, 34.6 g (67.3%) of the title compound were isolated.

$^1$H NMR (500 MHz, $d_6$-DMSO): δ 8.14 (s, 1H), 7.11 (d, J=3.6 Hz, 1H), 6.57 (d, J=3.6 Hz, 1H), 4.96 (q, J=6.0 Hz, 1H), 4.00-3.90 (m, 2H), 3.80 (m, 2H), 3.51 (m, 1H), 3.32 (s, 3H), 2.80 ($Ab_q$, J=15.6 Hz, 2H), 2.71 ($Ab_q$, J=15.6 Hz, 2H), 2.52-2.50 (m, 1H), 2.45-2.41 (m, 1H), 1.81 (m, 1H), 1.69-1.65 (m, 1H), 1.04 (d, J=6.9 Hz, 3H).

Example 15

Preparation of 2,4-dichloro-7H-pyrrolo[2,3-d]pyrimidine

A reactor was equipped with 7H-pyrrolo[2,3-d]pyrimidine-2,4-diol (10.0 g, 66.2 mmol) and toluene (30 ml) with stirring. Phosphorusoxychloride (18.5 ml, 198.5 mmol) was added and the reactor was warmed to 70° C. Diisopropylethylamine (23.0 m, 132.3 mmol) was added over 2.5 h to control the exotherm. After completion of the base addition, the reactor was heated to 106° C. and stirred at temperature for 16 h. The mixture was cooled to 25° C. and added slowly to a flask containing water (230 ml) and ethyl acetate (120 ml) at room temperature, then stirred overnight at room temperature. After filtration through Celite, the layers were separated the aqueous layer was extracted with ethyl acetate (3×75 ml). The organic layers were combined and washed with brine (100 ml). Darco KBB (1.24 g) was added to the organics, then filtered through Celite and dried over sodium sulfate (10.0 g). The solution was concentrated in vacuo to obtain the title compound (52% yield).

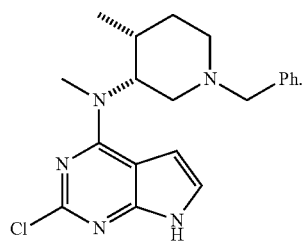

What is claimed is:
1. A compound of the Formula IVb